United States Patent
Harale et al.

(10) Patent No.: US 10,239,763 B1
(45) Date of Patent: Mar. 26, 2019

(54) SYSTEM FOR TAIL GAS TREATMENT OF SULFUR RECOVERY UNITS

(71) Applicant: Saudi Arabian Oil Company, Dhahran (SA)

(72) Inventors: Aadesh Harale, Abqaiq (SA); Mourad Younes, Abqaiq (SA); Maytham Musawi, Alhasa (SA)

(73) Assignee: SAUDI ARABIAN OIL COMPANY (SA)

( * ) Notice: Subject to any disclaimer, the term of this patent is extended or adjusted under 35 U.S.C. 154(b) by 0 days.

(21) Appl. No.: 15/832,136

(22) Filed: Dec. 5, 2017

(51) Int. Cl.
| | |
|---|---|
| *C01F 11/46* | (2006.01) |
| *C01B 17/04* | (2006.01) |
| *B01J 8/18* | (2006.01) |
| *B01J 8/00* | (2006.01) |
| *B01J 8/26* | (2006.01) |
| *C10L 3/10* | (2006.01) |
| *C07C 7/11* | (2006.01) |
| *B01D 53/52* | (2006.01) |

(52) U.S. Cl.
CPC .............. *C01F 11/46* (2013.01); *B01D 53/52* (2013.01); *B01J 8/005* (2013.01); *B01J 8/1827* (2013.01); *B01J 8/26* (2013.01); *C01B 17/0417* (2013.01); *C07C 7/11* (2013.01); *C10L 3/103* (2013.01); *B01D 2251/102* (2013.01); *B01D 2251/404* (2013.01); *B01D 2251/602* (2013.01); *B01D 2251/606* (2013.01); *C10L 2290/541* (2013.01)

(58) Field of Classification Search
CPC .......... C01F 11/46; C01F 11/06; C01B 17/04; C01B 17/0404; C01B 17/43; B01J 8/18; B01J 8/00; B01J 8/26; C10L 3/10; C07C 7/11; B01D 53/52; B01D 53/83
See application file for complete search history.

(56) References Cited

U.S. PATENT DOCUMENTS

| | | | |
|---|---|---|---|
| 8,277,736 B2* | 10/2012 | Proll .................... | B01J 8/1818 422/129 |
| 9,089,826 B2* | 7/2015 | Proell ................... | B01J 8/0055 |
| 9,927,118 B2* | 3/2018 | Gauthier ................ | C10J 3/725 |
| 2013/0125462 A1* | 5/2013 | Greiner ................. | F23C 10/005 48/61 |
| 2016/0017799 A1* | 1/2016 | Hoteit ................... | F02C 3/22 60/780 |

\* cited by examiner

*Primary Examiner* — Timothy C Vanoy
(74) *Attorney, Agent, or Firm* — Bracewell LLP; Constance Gall Rhebergen

(57) ABSTRACT

A process for recovering sulfur from a tail gas stream comprising the steps of providing a tail gas stream to a chemical looping combustion (CLC) unit, the tail gas stream comprising a sulfide component, providing an oxygen carrier to the CLC unit, the oxygen carrier comprising a calcium carbonate, providing an air stream to the CLC unit, the air stream comprising oxygen, and reacting the sulfide component in the CLC unit with the calcium compound and the air to produce a product effluent, the product effluent comprising calcium sulfate.

20 Claims, 5 Drawing Sheets

SYSTEM FOR TAIL GAS TREATMENT OF SULFUR RECOVERY UNITS

TECHNICAL FIELD

Disclosed are systems and methods for removing sulfur compounds. More specifically, disclosed are systems and methods for removing sulfur compounds from a tail gas stream of a sulfur recovery unit.

BACKGROUND

The removal of sour gas or acid gas components such as hydrogen sulfide ($H_2S$), carbon dioxide ($CO_2$), carbonyl sulfide (COS), carbon disulfide ($CS_2$) and mercaptans (RSH) from gas and liquid hydrocarbon streams is a process requirement in many parts of the hydrocarbon processing industry. Increasingly stringent environmental restrictions coupled with the need to process natural gas and crude oil with significant levels of sulfur requires sulfur recovery processes that can achieve high levels of conversion of hydrogen sulfide to elemental sulfur. The most common conversion method used is the Claus process. Approximately 90 to 95 percent (%) of recovered sulfur is produced by the Claus process.

The Claus process or Claus unit includes a thermal stage and a catalytic stage. The thermal stage can include a furnace, where hydrogen sulfide is reacted with oxygen to form sulfur dioxide ($SO_2$) at high temperatures, such as temperatures greater than 800 degrees Celsius (deg C.). Hydrogen sulfide and sulfur dioxide can react in the thermal stage to form elemental sulfur and steam. The process gases from the thermal stage can be cooled and the elemental sulfur can be separated from the other gases. The separated process gases can be routed to the catalytic stage. In the catalytic stage, catalytic reactions occur at lower temperatures (as compared to the thermal stage) in two to three catalytic reactors, such that further elemental sulfur recovery is achieved. The Claus process typically recovers 95% to 97% of the hydrogen sulfide in the feed stream.

The Claus process is less efficient when the feed stream contains hydrogen sulfide concentrations less than 40% and can require oxygen enriched air or additional thermal and catalytic stages to reach higher sulfur recovery. Additionally, low hydrogen sulfide concentrations can require reactors with larger volumes to handle the oxygen concentration in the air.

A treatment unit can be placed upstream of the Claus unit to first recover hydrogen sulfide from a sour gas. The tail gas from the catalytic stage can be treated to increase sulfur recovery. Claus reaction thermodynamics allows only 70% of the sulfur to be recovered in the thermal stage and catalytic stages and subsequently tail gas treatment stages are required to reach target sulfur recovery. Selection of an appropriate and cost effective tail gas treatment process to follow existing Claus plants is a challenge facing refiners and natural gas plant owners around the world.

SUMMARY

Disclosed are systems and methods for removing sulfur compounds. More specifically, disclosed are systems and methods for removing sulfur compounds from a tail gas stream of a sulfur recovery unit.

In a first aspect, a process for recovering sulfur from a tail gas stream is provided. The process includes the steps of providing a tail gas stream to a chemical looping combustion (CLC) unit, where the tail gas stream includes a sulfide component, providing an oxygen carrier to the CLC unit, where the oxygen carrier includes calcium carbonate, providing an air stream to the CLC unit, where the air stream includes oxygen, and reacting the sulfide component in the CLC unit with the calcium carbonate and the oxygen to produce a product effluent, the product effluent includes calcium sulfate.

In certain aspects, the process further includes the steps of introducing the oxygen carrier to an air reactor of the CLC unit, introducing the air stream to the air reactor of the CLC unit, allowing the calcium carbonate to decompose in the air reactor to produce an air reactor effluent that includes calcium oxide, introducing the air reactor effluent to an air reactor separator that includes a solid-gas separation unit, separating calcium oxide from the air reactor effluent in the air reactor separator to produce an air reactor exhaust and an air reactor discharge, where the air reactor discharge includes the calcium oxide, introducing the air reactor discharge to a fuel reactor of the CLC unit, introducing the tail gas stream to the fuel reactor, reacting the calcium oxide and the hydrogen sulfide to produce a fuel reactor effluent, the fuel reactor effluent includes calcium sulfide and calcium carbonate, introducing the fuel reactor effluent to a fuel reactor separator that includes a solid-gas separation unit, separating the calcium sulfide and calcium carbonate from the fuel reactor effluent in the fuel reactor separator to produce a flue gas exhaust and a fuel reactor discharge, where the fuel reactor discharge includes the calcium sulfide and calcium carbonate, introducing the fuel reactor discharge to the air reactor, reacting the calcium sulfide and the oxygen in the air reactor to produce calcium sulfate, and withdrawing a product effluent from the air reactor discharge, the product effluent includes a fraction of the calcium sulfate. In certain aspects, the fuel reactor is operated at a fuel reaction pressure of atmospheric pressure, and further wherein the fuel reactor is operated at a fuel reaction temperature of 650 deg C. In certain aspects, the air reactor is operated at an air reaction pressure of atmospheric pressure, and further wherein the air reactor is operated at an air reaction temperature of 900 deg C. In certain aspects, the air reactor is a fluidized bed reactor packed with calcium carbonate, and further wherein the fuel reactor is a fluidized bed reactor packed with calcium carbonate.

In certain aspects, the process further includes the steps of introducing the oxygen carrier to a calciner unit of the CLC unit, calcining the calcium carbonate in the oxygen carrier to produce a calciner effluent that includes calcium oxide, introducing the calciner effluent to a calciner separator, the calciner separator includes a solid-gas separation unit, separating the calcium oxide from the calciner effluent in the calciner separator to produce a calciner exhaust and a calciner discharge, introducing the calciner discharge to a fuel reactor of the CLC unit, introducing the tail gas stream to the fuel reactor, reacting the calcium oxide and the hydrogen sulfide to produce a fuel reactor effluent, where the fuel reactor effluent includes calcium sulfide and calcium carbonate, introducing the fuel reactor effluent to a fuel reactor separator, the fuel reactor separator includes a solid-gas separation unit, separating the calcium sulfide and calcium carbonate from the fuel reactor effluent in the fuel reactor separator to produce a flue gas exhaust and a fuel reactor discharge, where the fuel reactor discharge includes the calcium sulfide and calcium carbonate, introducing the fuel reactor discharge to an air reactor of the CLC unit, reacting the calcium sulfide and the oxygen in the air reactor to produce an air reactor effluent, the air reactor effluent includes calcium sulfate, introducing the air reactor effluent to an air reactor separator, the air reactor separator includes a solid-gas separation unit, separating calcium oxide from the air reactor effluent in the air reactor separator to produce an air reactor exhaust and an air reactor outlet, where the air reactor outlet includes the calcium sulfate, withdrawing a product effluent from the air reactor outlet, the product effluent includes a fraction of the calcium sulfate. In certain aspects, the calciner unit is operated at a calciner reaction pressure of atmospheric pressure, and further wherein the calciner unit is operated at a calciner reaction temperature of 900 deg C.

In certain aspects, the process further includes the steps of introducing the oxygen carrier to a calciner unit of the CLC unit, calcining the calcium carbonate in the oxygen carrier to produce a calciner effluent, calciner effluent includes calcium oxide, introducing the calciner effluent to a calciner separator, the calciner separator includes a solid-gas separation unit, separating the calcium oxide from the calciner effluent in the calciner separator to produce a calciner exhaust and a calciner discharge, diverting a portion of the calciner discharge to produce a calciner slipstream, introducing the calciner discharge to a fuel reactor of the CLC unit, introducing the tail gas stream to the fuel reactor, reacting the calcium oxide and the hydrogen sulfide to produce a fuel reactor effluent, the fuel reactor effluent includes calcium sulfide and calcium carbonate, introducing the fuel reactor effluent to a fuel reactor separator, the fuel reactor separator includes a solid-gas separation unit, separating the calcium sulfide and calcium carbonate from the fuel reactor effluent in the fuel reactor separator to produce a flue gas exhaust and a fuel reactor discharge, where the fuel reactor discharge includes the calcium sulfide and calcium carbonate, introducing the flue gas exhaust and the calciner slipstream to a reducing reactor of the CLC unit, reacting the calcium oxide and hydrogen sulfide in the reducing reactor to produce a reducing reactor effluent, separating the reducing reactor effluent in a reducing reactor separator to produce an exhaust gases stream and a reducing reactor discharge, the reducing reactor separator includes a solid-gas separation unit, introducing the reducing reactor discharge to the calciner unit, introducing the fuel reactor discharge to an air reactor of the CLC unit, reacting the calcium sulfide and the oxygen in the air reactor to produce an air reactor effluent, the air reactor effluent includes calcium sulfate, introducing the air reactor effluent to an air reactor separator, the air reactor separator includes a solid-gas separation unit, separating calcium oxide from the air reactor effluent in the air reactor separator to produce an air reactor exhaust and an air reactor discharge, where the air reactor discharge includes the calcium sulfate, withdrawing a product effluent from the air reactor discharge, the product effluent includes a fraction of the calcium sulfate. In certain aspects, the fuel reactor is operated at a fuel reaction pressure of atmospheric pressure, and further wherein the fuel reactor is operated at a fuel reaction temperature of 830 deg C. In certain aspects, the reducing reactor is operated at a reducing pressure of atmospheric pressure, and further wherein the reducing reactor is operated at a reducing temperature of 650 deg C.

In certain aspects, the process further includes the steps of introducing an acid gas stream to a sulfur recovery unit, the acid gas stream includes hydrogen sulfide, introducing a sulfur recovery unit (SRU) air stream to the sulfur recovery unit, where the SRU air stream includes oxygen, introducing an SRU fuel stream to the sulfur recovery unit, and reacting an amount of the hydrogen sulfide in the sulfur recovery unit with oxygen to produce an elemental sulfur stream and the tail gas stream.

In certain aspects, the process further includes the steps of introducing a sour gas feed to a gas sweetening unit, the sour gas feed includes hydrogen sulfide, product gases, and combinations of the same, separating the hydrocarbons in the gas sweetening unit to produce a sales gas stream, the sales gas stream includes the product gases, collecting the hydrogen sulfide and the other gases in the acid gas stream, introducing the acid gas stream to a sulfur recovery unit, the acid gas stream includes hydrogen sulfide, introducing a sulfur recovery unit (SRU) air stream to the sulfur recovery unit, the SRU air stream includes oxygen, introducing an SRU fuel stream to the sulfur recovery unit, and reacting an amount of the hydrogen sulfide in the sulfur recovery unit with oxygen to produce an elemental sulfur stream and the tail gas stream.

In certain aspects, the process further includes the steps of introducing a sour gas feed to a gas sweetening unit, the sour gas feed includes hydrogen sulfide, product gases, and combinations of the same, separating the hydrocarbons in the gas sweetening unit to produce a sales gas stream, the sales gas stream includes the product gases, collecting the hydrogen sulfide and the other gases in the acid gas stream, introducing the acid gas stream to a membrane unit, the membrane unit includes a hydrogen sulfide selective membrane, separating the hydrogen sulfide from the acid gas stream in the membrane unit to produce a hydrogen sulfide rich acid gas and a hydrogen sulfide lean acid gas, where the hydrogen sulfide rich acid gas includes hydrogen sulfide, introducing the hydrogen sulfide rich acid gas to a sulfur recovery unit, introducing a sulfur recovery unit (SRU) air stream to the sulfur recovery unit, the SRU air stream includes oxygen, introducing an SRU fuel stream to the sulfur recovery unit, reacting an amount of the hydrogen sulfide in the sulfur recovery unit with oxygen to produce an elemental sulfur stream and a tail gas stream, mixing the tail gas stream and the hydrogen sulfide lean acid gas to produce a mixed gas stream, and introducing the mixed gas stream to the CLC unit.

In second aspect, a system for recovering sulfur from a tail gas stream is provided. The system includes an air reactor, where the air reactor operates at an air reaction temperature and an air reaction pressure, where the air reactor includes a fluidized bed reactor, where the fluidized bed includes calcium carbonate, an air reactor separator fluidly connected to the air reactor and a fuel reactor, the air reactor separator includes a solid-gas separation unit, the fuel reactor fluidly connected to the air reactor separator, where the fuel reactor operates at a fuel reaction temperature and fuel reaction pressure, where the fuel reactor includes a fluidized bed reactor, where the fluidized bed includes calcium carbonate, and a fuel reactor separator fluidly connected to the fuel reactor and the air reactor, the fuel reactor separator includes a solid-gas separation unit.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

DETAILED DESCRIPTION

Figure 1:
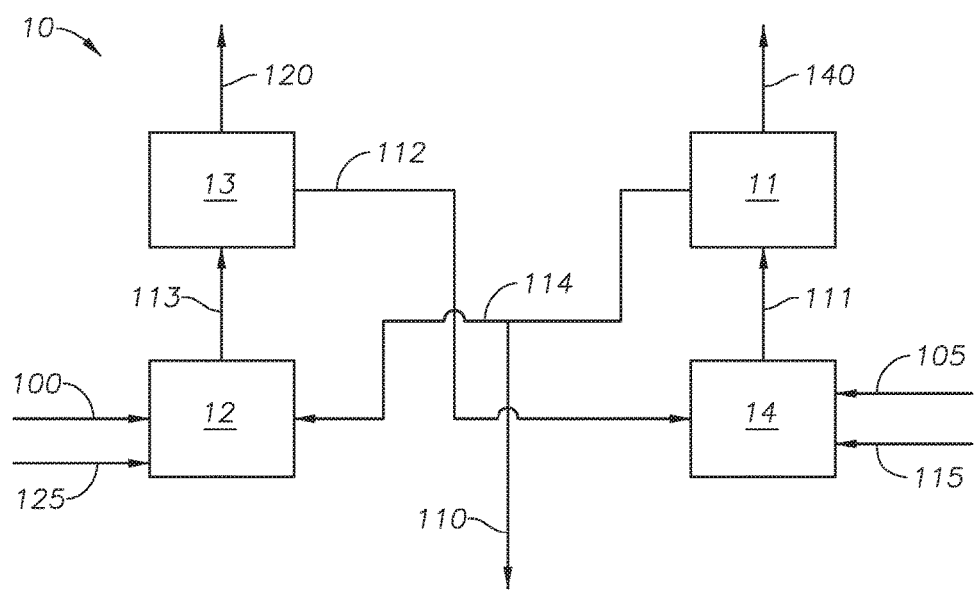
FIG. 1 is a process diagram of an embodiment of the sulfur recovery process.

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

The embodiments of the systems and methods of sulfur recovery described here are directed to the use of a chemical looping combustion (CLC) process to treat a tail gas stream from a Claus process. In a CLC process, a fuel reacts with a metal oxide in the reducer, the fuel reactor, so that the metal oxide is reduced to metal. Other reaction products in the reducer include carbon dioxide and steam. The metal exits the reducer and enters the combustor, the air reactor, where the metal reacts with air to regenerate the metal oxide. The metal oxides is then recycled back to the reducer. The heat of oxidation is carried by the oxidized metal and the high-temperature spent air from the air reactor. The spent air is used to produce steam that can be used as utility or to drive steam turbines for electricity generation. The reaction products depend on the reactants, the operating conditions, and the specific metal oxide employed in each reactor.

Advantageously, the systems and methods described address both feed streams with lower hydrogen sulfide concentrations and the need for tail gas treatment to meet environmental regulations. Advantageously, the systems and methods reduce the size of equipment across the entire sulfur recovery system. Advantageously, the systems and methods described here can be added to existing Claus processes. Advantageously, the systems and methods described here have increased efficiency compared to the conventional Claus process. Advantageously, the systems and methods described provide enhanced operation flexibility compared to conventional sulfur recovery processes. The systems and methods for sulfur recover provide enhanced operational flexibility compared to conventional processes. The systems and methods allow operation of the Claus unit at lower sulfur recovery levels, such as around 95%, while still meeting the emissions regulation limits.

As used throughout, "efficient" or "efficiency" refers to the energy consumption required to clean up the tail gas from a sulfur recovery unit.

As used throughout, "loop" or "loops" refers to the configuration of reactors in chemical looping combustion unit. The combination of fuel reactor, air reactor, calciner, reducing reactor, and combinations of the same.

As used throughout, "sulfur-containing compounds" includes sulfur-containing gaseous compounds other than hydrogen sulfide, sulfur dioxide, and elemental sulfur, naturally occurring or produced as part of an industrial process that can be removed from a gas stream in a sulfur recovery unit. Examples of sulfur-containing compounds can include carbonyl sulfide, carbon disulfide, sulfur trioxide, sulfur oxides (SOx), and combinations of the same.

As used throughout, "product gases" refers to gases which can be treated for sale or other industrial use. Examples of product gases include natural gas, light hydrocarbons, such as methane and ethane, air, and combinations of the same.

As used throughout, "sour gases" refers gases containing hydrogen sulfide and carbon dioxide.

As used throughout, "calcining" or "calcination" refers to removal of carbon dioxide in an endothermic reaction from calcium carbonate resulting in a calcium oxide product.

Referring to FIG. 1, a CLC unit suitable for use in the sulfur recovery process is described. CLC unit 10 contains a minimum of two fluidized bed reactors interconnected using loops. Oxygen carrier 105 can be introduced to air reactor 14 of CLC unit 10. Oxygen carrier 105 can include any oxygen carrier that reacts with sulfur. Examples of oxygen carriers can include calcium (Ca), iron (Fe), nickel (Ni), manganese (Mn), copper (Cu), and combinations of the same. In at least one embodiment, the oxygen carrier includes calcium. In at least one embodiment, the oxygen carrier includes calcium in the form of calcium carbonate ($CaCO_3$). In at least one embodiment, the oxygen carrier includes calcium in the form of calcium oxide (CaO). Advantageously, the use of calcium-based particles results in the sulfur compounds being trapped such that the calcium-based particles produce calcium-sulfur products. The oxygen in oxygen carrier 105 can be in a solid form. In at least one embodiment, oxygen carrier 105 is continuously introduced to CLC unit 10. In at least one embodiment, oxygen carrier 105 is introduced on an as needed-basis.

Air stream 115 can be introduced to air reactor 14 of CLC unit 10. Air stream 115 can be any source of air. Air stream 115 can include air, oxygen-enriched air, oxygen, or combinations of the same.

Air reactor 14 can be any type of bed reactor capable of supporting reactions containing oxygen, sulfur, and metals. In at least one embodiment, air reactor 14 is a fluidized bed reactor. The oxygen carrier can be loaded into air reactor 14 prior to the unit being placed in production. Air reactor 14 can operate at an air reaction temperature, an air reaction pressure, and an air reaction residence time. The air reaction temperature can be between 600 deg C. and 1300 deg C., alternately at or less than 900 deg C., and alternately between 500 deg C. and 890 deg C. Advantageously, maintaining an air reaction temperature at or less than 900 deg C. results in the oxidation of the oxygen carrier while reducing or suppressing the formation of nitrogen oxides ($NO_x$). The reactions in air reactor 14 can be exothermic. The air reaction pressure can be atmospheric pressure, alternately between 1 bar (100 kPa) and 10 bar (1000 kPa), and alternately between 1 bar (100 kPa) and 3 bar (300 kPa). The air reaction residence time can be between 1 second and 600 seconds and alternately between 80 seconds and 200 seconds.

Tail gas stream 100 can be introduced to fuel reactor 12 of CLC unit 10. Tail gas stream 100 can be the tail gas from any process unit containing hydrogen sulfide, sulfur dioxide, or combinations of the same. In at least one embodiment, tail gas stream 100 is produced by a Claus process.

Fuel stream 125 can be introduced to fuel reactor 12 of CLC unit 10. Fuel stream 125 can be any source of fuel that can be used in fuel reactor 12 to maintain the temperature. The reactions occurring in CLC unit 10 are endothermic requiring the addition of fuel to maintain the temperature. Examples of the fuel suitable for use in fuel stream 125 include combustible gases, liquid fuels, and solid fuels. In at least one embodiment, fuel stream 125 provides a combustible gas to maintain the temperature in fuel reactor 12. Examples of the combustible gas in fuel stream 125 include methane, carbon monoxide, hydrogen, fuel gases, and combinations of the same. In at least one embodiment, fuel stream 125 includes a combustible gas and has reduced complexity as compared to the use of a liquid fuel or solid fuel.

Fuel reactor 12 can operate at a fuel reaction temperature, a fuel reaction pressure, and a fuel reaction residence time. The fuel reaction temperature can be equal to or less than 900 deg C., alternately between 850 deg C. and 900 deg C., alternately between 800 deg C. and 850 deg C., alternately between 750 deg C. and 800 deg C., alternately between 700 deg C. and 750 deg C., alternately between 650 deg C. and 700 deg C., alternately equal to or less than 600 deg C. In at least one embodiment the fuel reaction temperature is 650 deg C. The fuel reaction pressure can be atmospheric pressure. The fuel reaction residence time can be between 1 second and 700 seconds and alternately between 50 seconds and 400 seconds.

The following describes the process and reactions occurring in CLC unit 10 when the oxygen carrier is calcium carbonate. While the process and reactions will be described along a linear path beginning with the oxygen carrier, one of skill in the art will understand that after a start-up period, the reactants and products will circulate through the CLC unit in a continuous loop except those products withdrawn as described. To the extent a stream is described as containing or including specific components, it is understood that any of the components (reactants or products listed in reactions 1-38) can be present and only certain components are noted. Multiple and competing reactions, as described, can be occurring simultaneously in both reactors.

Oxygen carrier 105 includes calcium in the form of calcium carbonate. In air reactor 14, the calcium carbonate decomposes to form calcium oxide (CaO) and carbon dioxide according to the following equation:

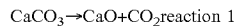CaCO$_3$→CaO+CO$_2$      reaction 1

Reaction 1 is an endothermic reaction with a change in enthalpy (ΔH) of positive 178 kilojoules per mole (kJ/mol). While individual reactions in air reactor 14 can be endothermic, the overall change in enthalpy in air reactor 14 is negative (exothermic). The calcium oxide is in solid form. Air reactor effluent 111 containing the products formed in air reactor 14 are introduced to air reactor separator 11. The solid products, including the calcium oxide are entrained in the gases in air reactor effluent 111 and carried to air reactor separator 11.

Air reactor separator 11 can be any type of separation unit capable of separating solids from gases. In at least one embodiment air reactor separator 11 is a cyclone separation unit. The gases separated in air reactor separator 11 exit the system as air reactor exhaust 140. Air reactor exhaust 140 can include carbon dioxide, nitrogen, argon, and combinations of the same. In at least one embodiment, air reactor exhaust 140 is in the absence of nitrogen oxides. Although described as a separate unit, one of skill in the art understands that the air reactor separator can be physically connected to the air reactor or be built into the air reactor.

The solids separated in air reactor separator 11 exit as air reactor discharge 114 and can be introduced to fuel reactor 12. Air reactor separator 11 and fuel reactor 12 can be designed and arranged to aid in transport of the solids from air reactor separator 11 to fuel reactor 12 by air reactor discharge 114. In at least one embodiment, air reactor discharge 114 contains only solids. In fuel reactor 12, the calcium oxide can react with the hydrogen sulfide in tail gas stream 100 to produce calcium sulfide (CaS) and water (H$_2$O) according to the following reaction:

CaO+H$_2$S→CaS+H$_2$O      reaction 2

Reaction 2 is exothermic with a ΔH of negative 59.44 kJ/mol. Additional reactions that can occur in fuel reactor 12, can include:

CaO+CO$_2$→CaCO$_3$      reaction 3

CaO+SO$_2$+0.5O$_2$↔CaSO$_4$      reaction 4

CaO+SO$_2$↔CaSO$_3$      reaction 5

CaO+SO$_3$↔CaSO$_4$      reaction 6

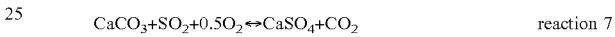CaCO$_3$+SO$_2$+0.5O$_2$↔CaSO$_4$+CO$_2$      reaction 7

CaCO$_3$+H$_2$S↔CaS+CO$_2$+H$_2$O      reaction 8

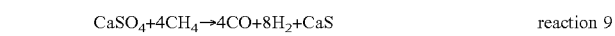CaSO$_4$+4CH$_4$→4CO+8H$_2$+CaS      reaction 9

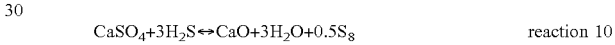CaSO$_4$+3H$_2$S↔CaO+3H$_2$O+0.5S$_8$      reaction 10

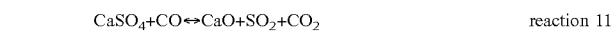CaSO$_4$+CO↔CaO+SO$_2$+CO$_2$      reaction 11

CaSO$_3$+0.5O$_2$↔CaSO$_4$      reaction 12

CaS+1.5O$_2$↔CaO+SO$_2$      reaction 13

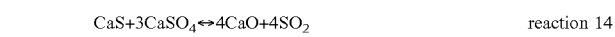CaS+3CaSO$_4$↔4CaO+4SO$_2$      reaction 14

CaS+2SO$_2$↔CaSO$_4$+S$_2$      reaction 15

CaS+CO$_2$↔CaO+COS      reaction 16

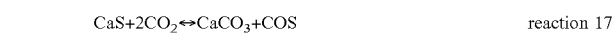CaS+2CO$_2$↔CaCO$_3$+COS      reaction 17

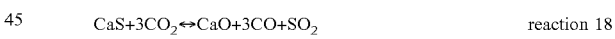CaS+3CO$_2$↔CaO+3CO+SO$_2$      reaction 18

CaS+4CO$_2$↔CaSO$_4$+4CO      reaction 19

2CaS+CO$_2$↔CS$_2$+CaO      reaction 20

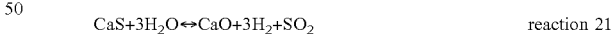CaS+3H$_2$O↔CaO+3H$_2$+SO$_2$      reaction 21

CaS+COS↔CS$_2$+2CaO      reaction 22

H$_2$S+0.5O$_2$↔H$_2$O+1/nS$_n$      reaction 23

H$_2$S+1.5O$_2$↔H$_2$O+SO$_2$      reaction 24

H$_2$S+CO↔COS+H$_2$      reaction 25

H$_2$S+CO$_2$↔COS+H$_2$O      reaction 26

2H$_2$S+CO$_2$↔CS$_2$+2H$_2$O      reaction 27

2H$_2$S+3O$_2$↔2SO$_2$+2H$_2$O      reaction 28

2H$_2$S+SO$_2$↔3S+2H$_2$O      reaction 29

S$_2$+CO$_2$↔COS+SO$_2$      reaction 30

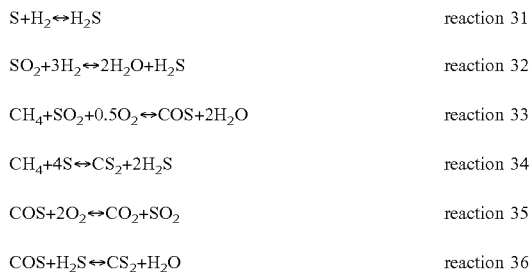

where $O_2$ is oxygen, $SO_3$ is sulfur trioxide, $CaSO_3$ is calcium sulfite, $CaSO_4$ is calcium sulfate, $CO$ is carbon monoxide, $CH_4$ is methane, $H_2$ is hydrogen, and $S_n$ refers to elemental sulfur, where n=a number between 1 and 8 inclusive. It should be noted that sulfur dioxide can react with calcium oxide to produce calcium sulfite and calcium sulfate, such as in reactions 4-6.

While individual reactions in fuel reactor 12 can be exothermic, the overall change in enthalpy in fuel reactor 12 is positive (endothermic). The total change in enthalpy is limited by the amount of fuel in tail gas stream 100 and the amount of fuel in fuel stream 125.

Fuel reactor effluent 113 can contain calcium sulfide (from reaction 2) and calcium carbonate (from reaction 3). Fuel reactor effluent 113 exits fuel reactor 12 and is introduced to fuel reactor separator 13.

Fuel reactor separator 13 can be any type of separation unit capable of separating solids from gases. In at least one embodiment fuel reactor separator 13 is a cyclone separation unit. The gases separated in fuel reactor separator 13 exit the system as flue gas exhaust 120. Flue gas exhaust 120 can contain steam and flue gases. Flue gases can include nitrogen, carbon dioxide, oxygen, particulate matter, carbon monoxide, nitrogen oxides, sulfur oxides, and combinations of the same.

The remaining gases and solids, including calcium sulfide and calcium carbonate exit the fuel reactor separator as fuel reactor discharge 112. Fuel reactor discharge 112 can be introduced to air reactor 14. Fuel reactor separator 13 and air reactor 14 can be designed and arranged to aid and facilitate transport of the solids from fuel reactor separator 13 to air reactor 14 by fuel reactor discharge 112. In at least one embodiment, fuel reactor discharge 112 contains only solids. In air reactor 14, the calcium sulfide can be oxidized with oxygen from air stream 115 to form calcium sulfate ($CaSO_4$) according to the following reactions:

CaS+2O$_2$→CaSO$_4$      reaction 37

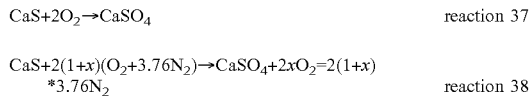

where $N_2$ is nitrogen.

The calcium sulfate can be in the form of solid particles. The calcium sulfate can be entrained in air reactor effluent 111 and introduced to air reactor separator 11. The calcium sulfate can exit air reactor separator 11 in air reactor discharge 114 and be introduced to fuel reactor 12.

A slipstream can be removed from air reactor discharge 114 as product effluent 110. Any means of separating a fraction of solids can be used to remove product effluent 110. In at least one embodiment, the means of separating a fraction of solids can be a valve. Product effluent 110 can include a fraction of the solids in air reactor discharge 114. The solids in product effluent 110 can include calcium sulfate, calcium oxide, calcium carbonate, and combinations of the same. In at least one embodiment, product effluent 110 includes calcium sulfate. The fraction of the solids removed in product effluent 110 from air reactor discharge 114 can be between 10 weight percent (wt %) and 30 wt %, alternately between 10 wt % and 25 wt %, alternately between 10 wt % and 20 wt %, alternately between 10 wt % and 15 wt %, and alternately between 12 wt % and 15 wt %. The flow rate of product effluent can be regulated through an instrumentation control loop to adjust the temperature in fuel reactor 12. The instrumentation control loop can include a valve that opens to allow flow in product effluent 110 and a temperature gauge in fuel reactor 12. The calcium sulfate in product effluent 110 can be used to produce cement.

It can be understood that reaction 1, reaction 37, and reaction 38 can occur at the same time in air reactor 14 after tail gas stream 100 has been introduced to CLC unit 10 and the reactants have completed a first loop through air reactor 14 and fuel reactor 12. One of skill in the art will understand that reactions 1-38 can compete with each other depending on the reaction kinetics of each reaction.

Figure 2:
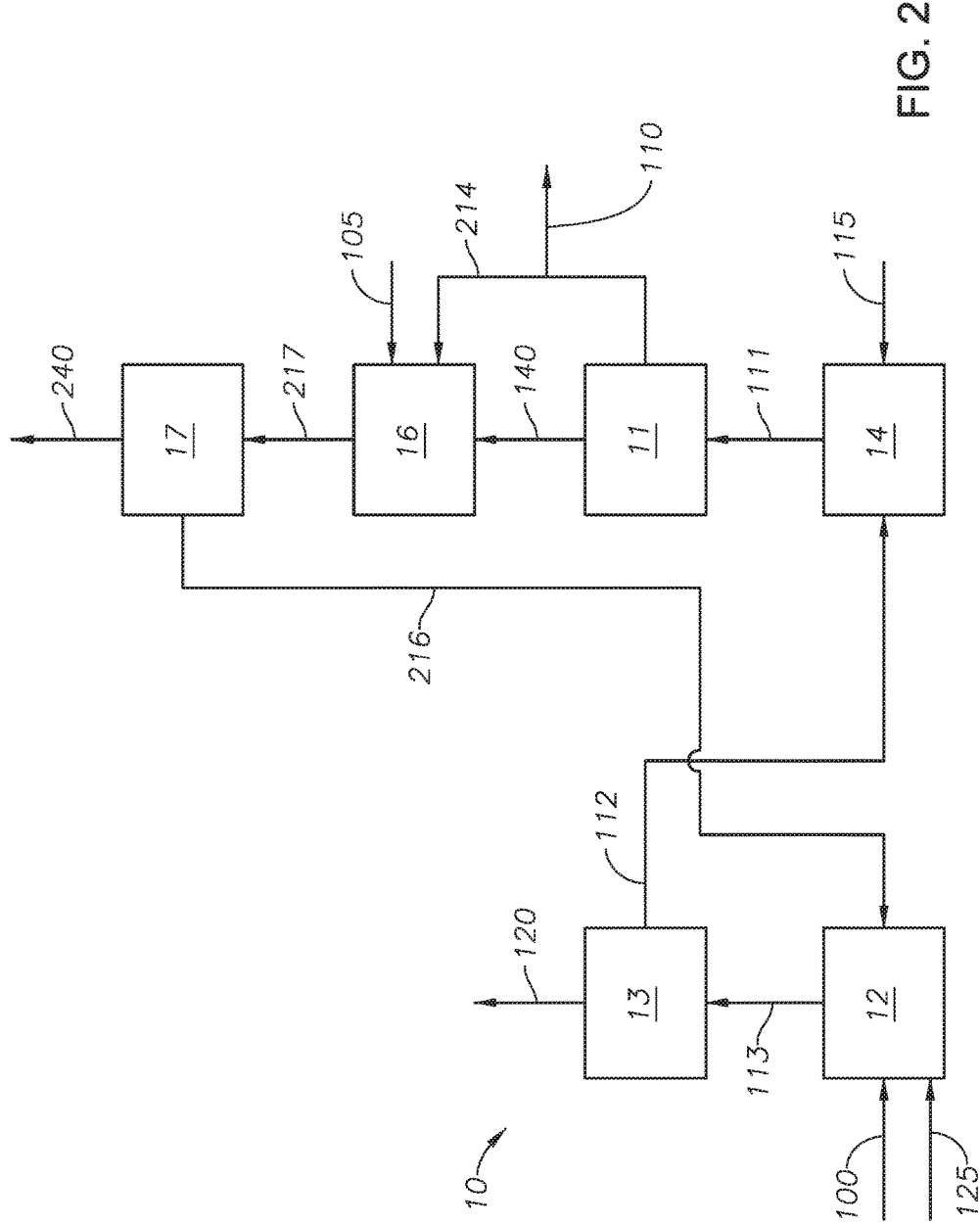
FIG. 2 is a process diagram of an embodiment of the sulfur recovery process.

Referring to FIG. 2, with reference to FIG. 1, an embodiment of the chemical looping combustion unit is provided.

Oxygen carrier 105 can be introduced to calciner unit 16. Calciner unit 16 can be any type of calciner unit capable of calcining calcium carbonate. Calciner unit 16 can operate at a calciner reaction temperature, a calciner reaction pressure, and a calciner reaction residence time. The calciner reaction temperature can be between 800 deg C. and 1300 deg C. and alternately between 850 deg C. and 950 deg C. In at least one embodiment, the calciner reaction temperature is 900 deg C. The calciner reaction pressure can be between 1 bar (100 kPa) and 5 bar (500 kPa). The calciner reaction residence time can be between 1 second and 600 seconds and alternately between 80 seconds and 200 seconds.

The following describes the process and reactions occurring in CLC unit 10 with the inclusion of calciner unit 16, when the oxygen carrier is calcium carbonate and with reference to FIG. 1. While the process and reactions will be described along a linear path, one of skill in the art will understand that after a start-up period, the reactants and products will circulate through the CLC unit in a continuous loop except those products withdrawn as described. Multiple and competing reactions, as described, can be occurring simultaneously in both reactors.

In calciner unit 16, the calcium carbonate can form calcium oxide and carbon dioxide according to reaction 1. The products can exit calciner unit 16 as calciner effluent 217. Calciner effluent 217 can include calcium oxide, carbon dioxide, nitrogen, and combinations of the same. Calciner effluent 217 can be introduced to calciner separator 17.

Calciner separator 17 can be any type of separation unit capable of separating solids from gases. In at least one embodiment calciner separator 17 is a cyclone separation unit. The gases separated in calciner separator 17 can exit CLC unit 10 as calciner exhaust 240. Calciner exhaust 240 can include nitrogen, carbon dioxide, oxygen, and combinations of the same.

The solids separated in calciner separator exit as calciner discharge 216. Calciner discharge 216 can include calcium oxide. Calciner discharge 216 can be introduced to fuel reactor 12.

Air reactor separator 11 can separate air reactor effluent 111 into air reactor exhaust 140 and air reactor outlet 214. Air reactor exhaust 140 can be introduced to calciner unit 16. Air reactor outlet 214 can contain calcium sulfate, calcium carbonate, calcium oxide, and combinations of the same. In at least one embodiment, air reactor outlet 214 can have a different composition than air reactor discharge 114, such as less calcium oxide, less calcium carbonate, and a greater amount of calcium sulfate. In at least one embodiment, the system described with reference to FIG. 2 can result in increased oxidation and reduced temperatures as compared to the system as described with reference to FIG. 1. Air reactor outlet 214 can be introduced to calciner unit 16. Product effluent 110 can be separated from air reactor outlet 214.

The addition of the calciner unit enables flexible operation of the CLC unit by providing the ability to adjust the operating conditions in each unit. By being able to adjust the operating conditions in the units, the system experiences reduced losses of calcium oxide and enhanced system energy efficiency.

Figure 3:
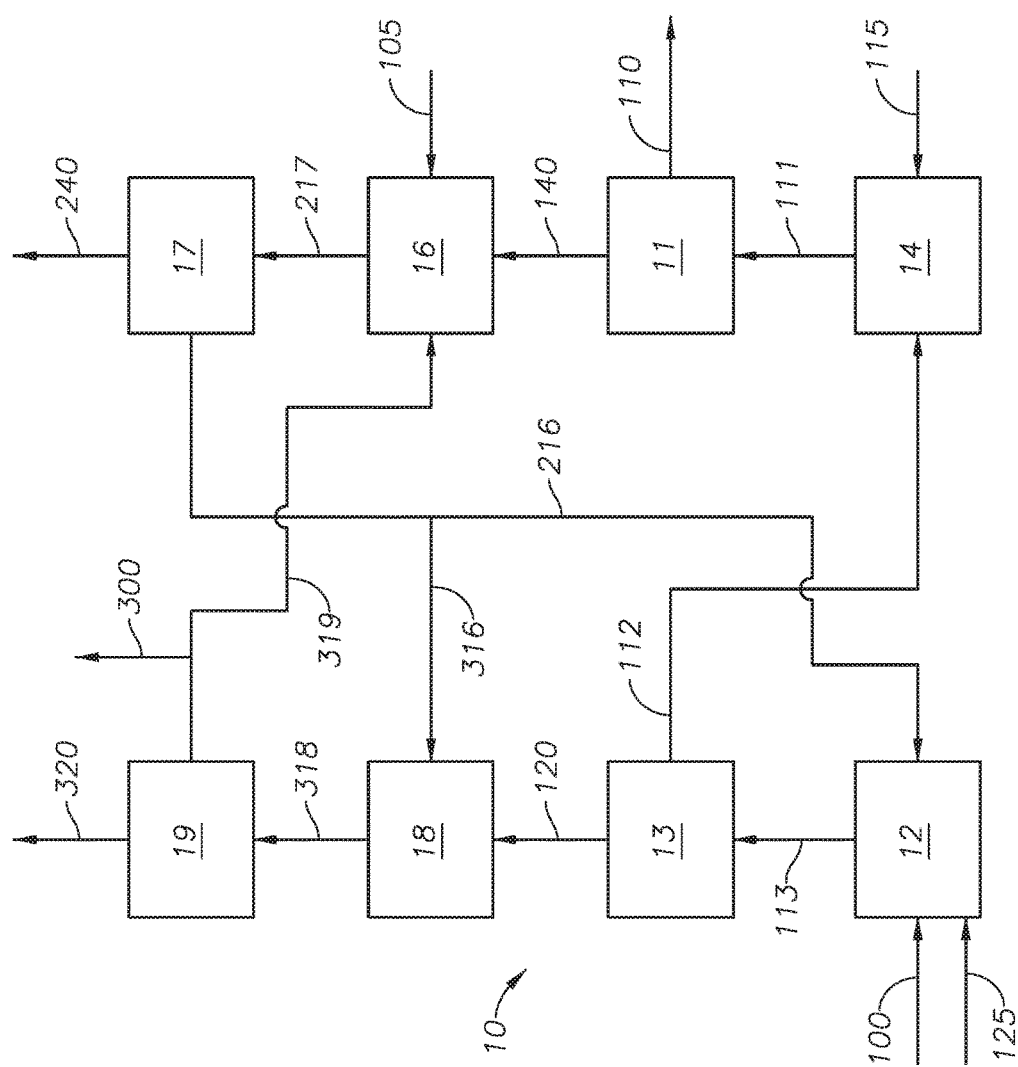
FIG. 3 is a process diagram of an embodiment of the sulfur recovery process.

Referring to FIG. 3, with reference to FIGS. 1 and 2, an embodiment of CLC unit 10 is provided that includes reducing reactor 18. The following describes the process and reactions occurring in CLC unit 10 with the inclusion of calciner unit 16 and reducing reactor 18, when the oxygen carrier is calcium carbonate and with reference to FIG. 1. While the process and reactions will be described along a linear path, one of skill in the art will understand that after a start-up period, the reactants and products will circulate through the CLC unit in a continuous loop except those products withdrawn as described. Multiple and competing reactions, as described, can be occurring simultaneously in both reactors.

In the embodiment shown with respect to FIG. 3, fuel reactor separator 13 separates air reactor effluent 113 into flue gas exhaust 120 and fuel reactor discharge 112. In an embodiment of CLC unit 10 that includes reducing reactor 18, fuel reactor 12 can operate at a fuel reaction temperature of 830 deg C. and a fuel reaction pressure of atmospheric pressure. Advantageously, operating fuel reactor 12 at a fuel reaction temperature of 830 deg C. results in calcium oxide selectively reacting with hydrogen sulfide, reaction 2. The fuel reaction temperature of 830 deg C. minimizes the carbon dioxide carbonation reaction, shown as follows:

$$CaO + CO_2 \rightarrow CaCO_3 \qquad \text{reaction 39}$$

Flue gas exhaust 120 can be introduced to reducing reactor 18.

Calciner slipstream 316 can be separated from calciner discharge 216. Calciner slipstream 316 can include a fraction of the solids in calciner discharge 216. The solids in calciner slipstream 316 can include calcium sulfate, calcium oxide, calcium carbonate, and combinations of the same. In at least one embodiment, calciner slipstream 316 includes calcium sulfate. The fraction of the solids removed in calciner slipstream 316 from calciner discharge 216 can be between 5 weight percent (wt %) and 20 wt %, alternately between 8 wt % and 15 wt %, and alternately between 10 wt % and 12 wt %. The fraction of solids removed in calciner slipstream 316 can be controlled by an instrumentation loop that controls the temperature of flue exhaust 120. The temperature of flue exhaust 120 is indicative of the operating conditions and the extent of conversion in reducing reactor 18. Based on the temperature of flue exhaust 120, the amount of solids entering reducing reactor 18 can be controlled by the weight in calciner slipstream 316. Calciner slipstream 316 can be introduced to reducing reactor 18. Reactions 2-36 occur in reducing reactor 18 with reactants from calciner slipstream 316 and flue gas exhaust 120.

Reducing reactor 18 can operate at a reducing temperature, a reducing pressure, and a reducing reactor residence time. The reducing temperature can be equal to or less than 900 deg C., alternately between 850 deg C. and 900 deg C., alternately between 800 deg C. and 850 deg C., alternately between 750 deg C. and 800 deg C., alternately between 700 deg C. and 750 deg C., alternately between 650 deg C. and 700 deg C., alternately equal to or less than 600 deg C. In at least one embodiment, the reducing temperature in reducing reactor 18 is 650 deg C. The reducing pressure can be atmospheric pressure. The reducing reactor residence time can be between 1 second and 700 seconds and alternately between 50 seconds and 400 seconds. Operating reducing reactor 18 at temperatures lower than fuel reactor 12 increases the efficiency of reducing reactor 18 and suppresses side reactions. Reducing reactor effluent 318 can be introduced to reducing reactor separator 19.

Reducing reactor separator 19 can be any type of separation unit capable of separating solids from gases. In at least one embodiment reducing reactor 19 is a cyclone separation unit. The gases separated in reducing reactor separator 19 exit CLC unit 10 as exhaust gases stream 320. Exhaust gases stream 320 can include steam and trace amounts of hydrogen sulfide. The trace amounts of hydrogen sulfide level in exhaust gases stream 320 can be less than 1 part-per-million by volume (ppmv). Reducing reactor discharge 319 contains the solids separated from reducing reactor effluent 318. Reducing reactor discharge 319 can include calcium carbonate, calcium sulfide, and combinations of the same. Reducing reactor discharge 319 can be introduced to calciner unit 16. Purge stream 300 can be withdrawn from reducing reactor discharge 319. Purge stream 300 can include a fraction of the solids in reducing reactor discharge 319. The solids in purge stream 300 can include calcium sulfate, calcium oxide, calcium carbonate, and combinations of the same. In at least one embodiment, purge stream 300 includes calcium sulfate, calcium oxide, and combinations of the same. The fraction of the solids removed in purge stream 300 from reducing reactor discharge 319 can be between 5 weight percent (wt %) and 20 wt %, alternately between 8 wt % and 15 wt %, and alternately between 10 wt % and 12 wt %. The combination of fuel reactor 12 and reducing reactor 18 provides better control of the reaction conditions in each reactor, allowing the reaction conditions in each reactor to foster specific reactions to produce a purer product.

Employing reducing reactor 18 as part of CLC unit 10 allows CLC unit 10 to achieve greater than 99.5 wt % recovery of sulfur from hydrogen sulfide. Advantageously, the addition of reducing reactor 18 minimizes the need for solids circulation. In an ideal operating environment, the need for solids circulation would be eliminated as only calcium sulfate would be produced from CLC unit 10 with the addition of reducing reactor 18; in a real operating environment, the conversion can be thermodynamically limited requiring re-circulation of a minimal amount of solids.

Figure 4:
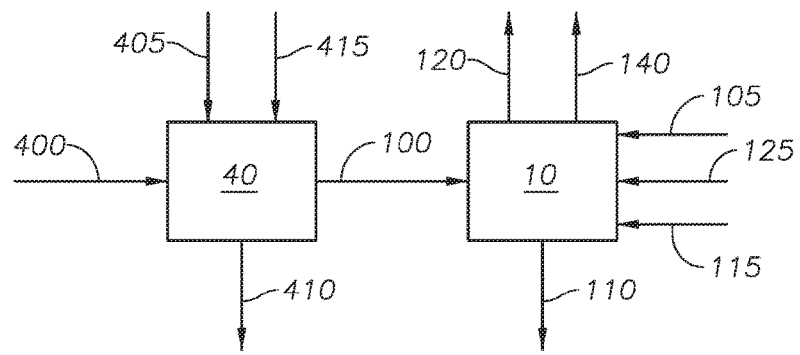
FIG. 4 is a process diagram of an embodiment of the sulfur recovery process.

Referring to FIG. 4, with reference to FIG. 1, an embodiment of a sulfur recovery process employing a CLC unit is provided. Acid gas stream 400 is introduced to sulfur recovery unit 40 along with sulfur recovery unit (SRU) fuel stream 405 and SRU air stream 415. Acid gas stream 400 can be any source of acid gas that comprises hydrogen sulfide. In at least one embodiment, acid gas stream 40 has a concentration of hydrogen sulfide between 25 wt % and 75 wt %. In at least one embodiment, acid gas stream 400 can include sulfur dioxide, hydrogen sulfide, carbon dioxide, sulfur-containing compounds, and combinations of the same.

SRU fuel stream 405 can be any source of fuel gas suitable for increasing the temperature of the combustion furnace (not shown) in sulfur recovery unit 40. SRU air stream 415 can be any source of oxygen containing gas suitable for use in the combustion furnace of sulfur recovery unit 40. SRU air stream 415 can include air, oxygen, oxygen-enriched air, and combinations of the same.

In sulfur recovery unit 40, the hydrogen sulfide in acid gas stream 400 and oxygen in SRU air stream 415 react to produce elemental sulfur stream 410 and tail gas stream 100. Elemental sulfur stream 410 can include liquid elemental sulfur. In at least one embodiment, sulfur recovery unit 40 can be a Claus process. Tail gas stream 100 can be introduced to CLC unit 10.

Figure 5:
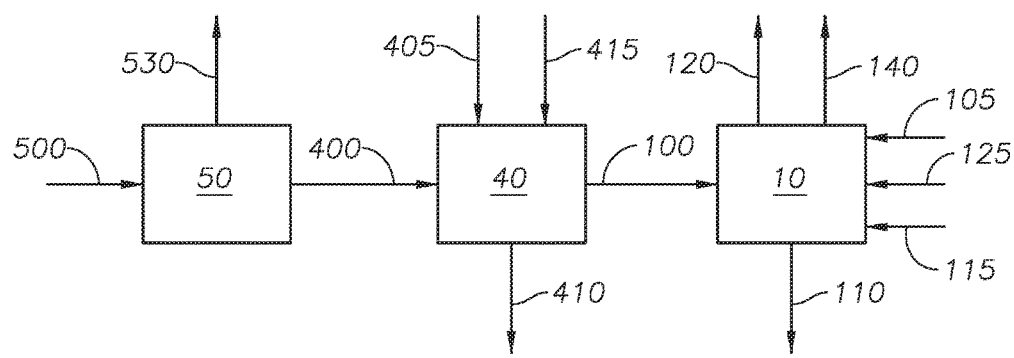
FIG. 5 is a process diagram of an embodiment of the sulfur recovery process.

Referring to FIG. 5, with reference to FIGS. 1 and 4, an embodiment of a sulfur recovery process employing a CLC unit and a gas sweetening unit is provided. Sour gas stream 500 can be introduced to gas sweetening unit 50. Sour gas stream 500 can be any gas stream containing sour gases and product gases. In at least one embodiment, sour gas stream 500 can include methane, hydrocarbons, hydrogen sulfide, carbon dioxide, and combinations of the same. In at least one embodiment, sour gas stream 500 can include 40% by volume or less hydrogen sulfide. Sour gas stream 500 is introduced to gas sweetening unit 50.

Gas sweetening unit 50 can be any unit capable of removing acid gases from a gas stream. Examples of gas sweetening units can include amine units. In at least one embodiment, gas sweetening unit 50 is an amine unit. Sour gas stream 500 is separated in gas sweetening unit 50 to produce sales gas stream 530 and acid gas stream 400. Sales gas stream 530 is a sweetened gas stream. Sales gas stream 530 can be sent for further processing, can be sent for storage, or can be sent for disposal. Acid gas stream 400 can be introduced to sulfur recovery unit 40.

Figure 6:
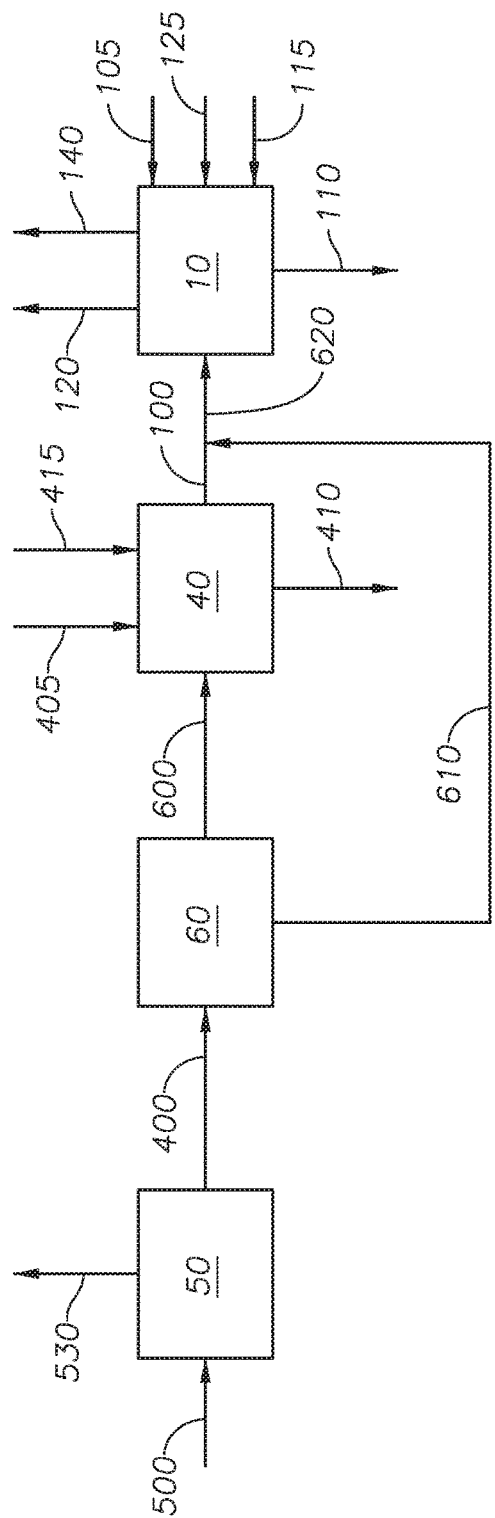
FIG. 6 is a process diagram of an embodiment of the sulfur recovery process.

Referring to FIG. 6, with reference to FIGS. 1, 4 and 5, an embodiment of a sulfur recovery process employing a CLC unit, a gas sweetening unit and a membrane unit is provided. Acid gas stream 400 can be introduced to membrane unit 60. Membrane unit 60 can include any membrane capable of separating hydrogen sulfide and carbon dioxide. In at least one embodiment, membrane unit 60 includes a carbon dioxide selective membrane. Membrane unit 60 separates acid gas stream 400 into hydrogen sulfide rich acid gas 600 and hydrogen sulfide lean acid gas 610.

Reducing the amount of carbon dioxide in hydrogen sulfide rich acid gas 600 is advantageous because the carbon dioxide can act as a diluent and reduce energy needed to heat the streams to the CLC unit.

Hydrogen sulfide rich acid gas 600 can contain hydrogen sulfide, carbon dioxide, and combinations of the same. In at least one embodiment, hydrogen sulfide rich acid gas 600 can contain other gases present in acid gas stream 400. Hydrogen sulfide rich acid gas 600 contains between 25 wt % and 85 wt % hydrogen sulfide. Hydrogen sulfide rich acid gas 600 can be introduced to sulfur recovery unit 40.

Hydrogen sulfide lean acid gas 610 can contain carbon dioxide, hydrogen sulfide, and combinations of the same. Hydrogen sulfide lean acid gas 610 contains between 5 wt % and 8 wt %. Hydrogen sulfide lean acid gas 610 can be mixed with tail gas stream 100 to produce mixed gas 620. Mixed gas 620 can be introduced to CLC unit 10.

The sulfur recovery processes and systems described here are in the absence of one or more thermal oxidizers. The sulfur recovery processes and systems described here are in the absence of a flue gas de-sulfurization system. Flue gas de-sulfurization systems can include a SCOT process, an ammonia process, wet scrubbing processes, and dry scrubbing processes. The addition of the CLC process can result in a Claus process that only requires two catalytic reactors in the catalytic stage. The sulfur recovery processes and systems described here are in the absence of process units that require a feed of hydrogen gas. The systems and process described here are in the absence of a CLC process employing calcium sulfate as an oxygen carrier.

EXAMPLE

Example 1

The first example simulated different embodiments of CLC unit 10 as described with reference to FIGS. 1, 2 and 3 in a process according to an embodiment described with reference to FIG. 5. The percentages are shown on a dry weight basis. The data are based on simulations performed using Aspen Plus®. Stream 114 and stream 216 are introduced to fuel reactor 12 depending on the embodiment. Stream 112 is introduced to air reactor 14. Stream 214 and Stream 319 are introduced to calciner unit 16.

TABLE 1

|  | Units | FIG. 1 | FIG. 2 | FIG. 3 |
|---|---|---|---|---|
| Overall sulfur recovery | Percent (%) | 99.94 | 99.93 | 99.92 |
| Sulfur recovery in CLC unit 10 | % | 98.8 | 98.78 | 98.57 |
| Stream 105 | kg/s | 3.5 | 2.1 | 2.1 |
| Stream 114 | kg/s | 52.2 | N/A | N/A |
| Stream 216 | kg/s | N/A | 38.6 | 0.8 |
| Stream 112 | kg/s | 65.3 | 48.2 | 1.0 |
| Stream 316 | kg/s | N/A | N/A | 13.3 |
| Stream 214 | kg/s | N/A | 2.1 | N/A |
| Stream 319 | kg/s | N/A | N/A | 24.0 |
| Stream 115 | kg/s | 2.6 | 2.6 | 2.6 |
| Fuel reaction temperature | deg C. | 650.0 | 650.0 | 790.0 |
| Reducing reaction temperature | deg C. | N/A | N/A | 650.0 |
| Air reaction temperature | deg C. | 900.0 | 900.0 | 900.0 |
| Calciner reaction temperature | deg C. | N/A | 900.0 | 900.0 |
| Fuel reactor 12 heat output | MW | 38.1 | 34.9 | −18.9 |
| Reducing reactor 18 heat output | MW | N/A | N/A | 45.2 |
| Air reactor 14 heat output | MW | −57.3 | −45.3 | 5.5 |
| Calciner unit 16 heat output | MW | N/A | −5.2 | −46.3 |
| Net Heat | MW | −19.1 | −15.7 | −14.5 |
| Stream 120 | | | | |
| Hydrogen sulfide | ppm | 163.8 | 163.8 | 345.0 |
| Sulfur dioxide | ppm | 12.7 | 12.7 | 978.0 |
| Carbonyl sulfide | ppm | 0.2 | 0.2 | 13.0 |
| Carbon dioxide | % | 1.6 | 1.6 | 27.0 |
| Stream 320 | | | | |
| Hydrogen sulfide | ppm | N/A | N/A | 218.3 |
| Sulfur dioxide | ppm | N/A | N/A | 17.1 |
| Carbonyl sulfide | ppm | N/A | N/A | 0.3 |
| Carbon dioxide | % | N/A | N/A | 2.1 |
| Stream 140 | | | | |
| Sulfur dioxide | ppm | 0.3 | 0.3 | 0.1 |
| Carbonyl sulfide | ppm | 0.0 | 0.0 | 0.0 |
| Carbon dioxide | % | 77.9 | 75.2 | 0.0 |
| Nitrogen | % | 21.9 | 24.6 | 97.9 |
| Stream 240 | | | | |
| Carbon dioxide | % | N/A | 76.9 | 74.3 |
| Purge Split % | % | 0.05000 | 0.05000 | 0.03000 |
| Purge CaCO3 flow | kg/s | 0.00000 | 0.00000 | 0.00633 |
| Purge CaO flow | kg/s | 1.38368 | 0.60534 | 0.00000 |

TABLE 1-continued

|  | Units | FIG. 1 | FIG. 2 | FIG. 3 |
|---|---|---|---|---|
| Stream 110 | kg/s | 1.36420 | 1.36387 | 0.00031 |
| Purge CaS flow | kg/s | 0.00000 | 0.00000 | 0.00002 |

Example 2

The second example simulated different embodiments of CLC unit 10 as described with reference to FIGS. 1, 2 and 3 in a process according to an embodiment described with reference to FIG. 6. The percentages are shown on a dry weight basis. Simulated using Aspen Plus®. Stream 114 and stream 216 are introduced to fuel reactor 12 depending on the embodiment. Stream 112 is introduced to the air reactor. Stream 214 and Stream 319 are introduced to calciner unit 16 depending on the embodiment.

TABLE 2

|  | Units | FIG. 1 | FIG. 2 | FIG. 3 |
|---|---|---|---|---|
| Overall sulfur recovery | Percent (%) | 99.94 | 99.94 | 99.42 |
| Sulfur recovery in CLC unit 10 | % | 99.80 | 99.80 | 99.81 |
| Stream 105 | kg/s | 10.3 | 10.0 | 7.0 |
| Stream 114 | kg/s | 57.2 | N/A | N/A |
| Stream 216 | kg/s | N/A | 61.9 | 3.1 |
| Stream 112 | kg/s | 77.8 | 72.3 | 3.9 |
| Stream 316 | kg/s | N/A | N/A | 18.5 |
| Stream 214 | kg/s | N/A | 10.0 | N/A |
| Stream 319 | kg/s | N/A | N/A | 33.7 |
| Stream 115 | kg/s | 16.6 | 17.6 | 20.0 |
| Fuel reaction temperature | deg C. | 650.0 | 650.0 | 900.0 |
| Reaction temperature | deg C. | N/A | N/A | 650.0 |
| Air reaction temperature | deg C. | 900.0 | 900.0 | 900.0 |
| Calciner reaction temperature | deg C. | N/A | 900.0 | 902.0 |
| Fuel reactor 12 heat output | MW | 43.9 | 45.0 | −19.7 |
| Reducing reactor 18 heat output | MW | N/A | N/A | 51.2 |
| Air reactor 14 heat output | MW | −44.0 | −20.1 | 34.9 |
| Calciner unit 16 heat output | MW | N/A | −25.1 | −58.8 |
| Net Heat | MW | −0.1 | −0.2 | 7.5 |
| Stream 120 |  |  |  |  |
| Hydrogen sulfide | Ppm | 188.3 | 188.3 | 712.9 |
| Sulfur dioxide | ppm | 12.7 | 12.7 | 1197.9 |
| Carbonyl sulfide | ppm | 0.2 | 0.2 | 39.0 |
| Carbon dioxide | % | 1.6 | 1.6 | 30.4 |
| Stream 320 |  |  |  |  |
| Hydrogen sulfide | ppm | N/A | N/A | 188.3 |
| Sulfur dioxide | ppm | N/A | N/A | 12.7 |
| Carbonyl sulfide | ppm | N/A | N/A | 0.2 |
| Carbon dioxide | % | N/A | N/A | 1.6 |
| Stream 140 |  |  |  |  |
| Sulfur dioxide | ppm | 0.1 | 0.2 | 0.1 |
| Carbonyl sulfide | ppm | 0.0 | 0.0 | 0.0 |
| Carbon dioxide | % | 41.1 | 30.6 | 0.0 |
| Nitrogen | % | 57.9 | 69.1 | 96.0 |
| Stream 240 |  |  |  |  |
| Carbon dioxide | % | N/A | 39.0 | 32.4 |
| Purge Split % | % | 0.15 | 0.15 | 0.05 |
| Purge CaCO3 flow | kg/s | 0.00000 | 0.00000 | 0.01096 |
| Purge CaO flow | kg/s | 2.7305 | 2.5747 | 0.00478 |
| Stream 110 | kg/s | 7.3625 | 7.3627 | 0.00022 |
| Purge CaS flow | kg/s | 0.00000 | 0.00000 | 0.00014 |

Although the embodiments have been described in detail, it should be understood that various changes, substitutions, and alterations can be made hereupon without departing from the principle and scope. Accordingly, the scope of the embodiments should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value to about another particular value and are inclusive unless otherwise indicated. When such a range is expressed, it is to be understood that another embodiment is from the one particular value to the other particular value, along with all combinations within said range.

As used here and in the appended claims, the words "comprise," "has," and "include" and all grammatical variations thereof are each intended to have an open, non-limiting meaning that does not exclude additional elements or steps.

That which is claimed is:

1. A process for recovering sulfur from a tail gas stream, the process comprising the steps of:
providing a tail gas stream to a chemical looping combustion (CLC) unit, where the tail gas stream comprises a sulfide component;
providing an oxygen carrier to the CLC unit, where the oxygen carrier comprises calcium carbonate;
providing an air stream to the CLC unit, where the air stream comprises oxygen; and
reacting the sulfide component in the CLC unit with the calcium carbonate and the oxygen to produce a product effluent, where the product effluent comprises calcium sulfate.

2. The process of claim 1, further comprising the steps of:
introducing the oxygen carrier to an air reactor of the CLC unit;
introducing the air stream to the air reactor of the CLC unit;
allowing the calcium carbonate to decompose in the air reactor to produce an air reactor effluent, the air reactor effluent comprises calcium oxide;
introducing the air reactor effluent to an air reactor separator, where the air reactor separator comprises a solid-gas separation unit;
separating calcium oxide from the air reactor effluent in the air reactor separator to produce an air reactor exhaust and an air reactor discharge, where the air reactor discharge comprises the calcium oxide;
introducing the air reactor discharge to a fuel reactor of the CLC unit;
introducing the tail gas stream to the fuel reactor;
reacting the calcium oxide and the hydrogen sulfide to produce a fuel reactor effluent, where the fuel reactor effluent comprises calcium sulfide and calcium carbonate;

introducing the fuel reactor effluent to a fuel reactor separator, where the fuel reactor separator comprises a solid-gas separation unit;

separating the calcium sulfide and calcium carbonate from the fuel reactor effluent in the fuel reactor separator to produce a flue gas exhaust and a fuel reactor discharge, where the fuel reactor discharge comprises the calcium sulfide and calcium carbonate;

introducing the fuel reactor discharge to the air reactor;

reacting the calcium sulfide and the oxygen in the air reactor to produce calcium sulfate; and withdrawing a product effluent from the air reactor discharge, where the product effluent comprises a fraction of the calcium sulfate.

3. The process of claim 2, wherein the fuel reactor is operated at a fuel reaction pressure of atmospheric pressure, and further wherein the fuel reactor is operated at a fuel reaction temperature of 650 deg C.

4. The process of claim 2, wherein the air reactor is operated at an air reaction pressure of atmospheric pressure, and further wherein the air reactor is operated at an air reaction temperature of 900 deg C.

5. The process of claim 2, wherein the air reactor is a fluidized bed reactor packed with calcium carbonate, and further wherein the fuel reactor is a fluidized bed reactor packed with calcium carbonate.

6. The process of claim 1, further comprising the steps of:

introducing the oxygen carrier to a calciner unit of the CLC unit;

calcining the calcium carbonate in the oxygen carrier to produce a calciner effluent, where the calciner effluent comprises calcium oxide;

introducing the calciner effluent to a calciner separator, where the calciner separator comprises a solid-gas separation unit;

separating the calcium oxide from the calciner effluent in the calciner separator to produce a calciner exhaust and a calciner discharge;

introducing the calciner discharge to a fuel reactor of the CLC unit;

introducing the tail gas stream to the fuel reactor;

reacting the calcium oxide and the hydrogen sulfide to produce a fuel reactor effluent, where the fuel reactor effluent comprises calcium sulfide and calcium carbonate;

introducing the fuel reactor effluent to a fuel reactor separator, where the fuel reactor separator comprises a solid-gas separation unit;

separating the calcium sulfide and calcium carbonate from the fuel reactor effluent in the fuel reactor separator to produce a flue gas exhaust and a fuel reactor discharge, where the fuel reactor discharge comprises the calcium sulfide and calcium carbonate;

introducing the fuel reactor discharge to an air reactor of the CLC unit;

reacting the calcium sulfide and the oxygen in the air reactor to produce an air reactor effluent, where the air reactor effluent comprises calcium sulfate;

introducing the air reactor effluent to an air reactor separator, where the air reactor separator comprises a solid-gas separation unit;

separating calcium oxide from the air reactor effluent in the air reactor separator to produce an air reactor exhaust and an air reactor outlet, where the air reactor outlet comprises the calcium sulfate;

withdrawing a product effluent from the air reactor outlet, where the product effluent comprises a fraction of the calcium sulfate.

7. The process of claim 6, wherein the fuel reactor is operated at a fuel reaction pressure of atmospheric pressure, and further wherein the fuel reactor is operated at a fuel reaction temperature of 650 deg C.

8. The process of claim 6, wherein the air reactor is operated at an air reaction pressure of atmospheric pressure, and further wherein the air reactor is operated at an air reaction temperature of 900 deg C.

9. The process of claim 6, wherein the calciner unit is operated at a calciner reaction pressure of atmospheric pressure, and further wherein the calciner unit is operated at a calciner reaction temperature of 900 deg C.

10. The process of claim 6, wherein the air reactor is a fluidized bed reactor packed with calcium carbonate, and further wherein the fuel reactor is a fluidized bed reactor packed with calcium carbonate.

11. The process of claim 1, further comprising the steps of:

introducing the oxygen carrier to a calciner unit of the CLC unit;

calcining the calcium carbonate in the oxygen carrier to produce a calciner effluent, where the calciner effluent comprises calcium oxide;

introducing the calciner effluent to a calciner separator, where the calciner separator comprises a solid-gas separation unit;

separating the calcium oxide from the calciner effluent in the calciner separator to produce a calciner exhaust and a calciner discharge;

diverting a portion of the calciner discharge to produce a calciner slipstream;

introducing the calciner discharge to a fuel reactor of the CLC unit;

introducing the tail gas stream to the fuel reactor;

reacting the calcium oxide and the hydrogen sulfide to produce a fuel reactor effluent, where the fuel reactor effluent comprises calcium sulfide and calcium carbonate;

introducing the fuel reactor effluent to a fuel reactor separator, where the fuel reactor separator comprises a solid-gas separation unit;

separating the calcium sulfide and calcium carbonate from the fuel reactor effluent in the fuel reactor separator to produce a flue gas exhaust and a fuel reactor discharge, where the fuel reactor discharge comprises the calcium sulfide and calcium carbonate;

introducing the flue gas exhaust and the calciner slipstream to a reducing reactor of the CLC unit;

reacting the calcium oxide and hydrogen sulfide in the reducing reactor to produce a reducing reactor effluent;

separating the reducing reactor effluent in a reducing reactor separator to produce an exhaust gases stream and a reducing reactor discharge, where the reducing reactor separator comprises a solid-gas separation unit;

introducing the reducing reactor discharge to the calciner unit;

introducing the fuel reactor discharge to an air reactor of the CLC unit;

reacting the calcium sulfide and the oxygen in the air reactor to produce an air reactor effluent, where the air reactor effluent comprises calcium sulfate;

introducing the air reactor effluent to an air reactor separator, where the air reactor separator comprises a solid-gas separation unit;

separating calcium oxide from the air reactor effluent in the air reactor separator to produce an air reactor exhaust and an air reactor discharge, where the air reactor discharge comprises the calcium sulfate;

withdrawing a product effluent from the air reactor discharge, where the product effluent comprises a fraction of the calcium sulfate.

12. The process of claim 11, wherein the fuel reactor is operated at a fuel reaction pressure of atmospheric pressure, and further wherein the fuel reactor is operated at a fuel reaction temperature of 830 deg C.

13. The process of claim 11, wherein the air reactor is operated at an air reaction pressure of atmospheric pressure, and further wherein the air reactor is operated at an air reaction temperature of 900 deg C.

14. The process of claim 11, wherein the calciner unit is operated at a calciner reaction pressure of atmospheric pressure, and further wherein the calciner unit is operated at a calciner reaction temperature of 900 deg C.

15. The process of claim 11, wherein the reducing reactor is operated at a reducing pressure of atmospheric pressure, and further wherein the reducing reactor is operated at a reducing temperature of 650 deg C.

16. The process of claim 11, wherein the air reactor is a fluidized bed reactor packed with calcium carbonate, and further wherein the fuel reactor is a fluidized bed reactor packed with calcium carbonate.

17. The process of claim 1, further comprising the steps of:
introducing an acid gas stream to a sulfur recovery unit, where the acid gas stream comprises hydrogen sulfide;
introducing a sulfur recovery unit (SRU) air stream to the sulfur recovery unit, where the SRU air stream comprises oxygen;
introducing an SRU fuel stream to the sulfur recovery unit; and
reacting an amount of the hydrogen sulfide in the sulfur recovery unit with oxygen to produce an elemental sulfur stream and the tail gas stream.

18. The process of claim 1, further comprising the steps of:
introducing a sour gas feed to a gas sweetening unit, where the sour gas feed comprises hydrogen sulfide, product gases, and combinations of the same;
separating the hydrocarbons in the gas sweetening unit to produce a sales gas stream, where the sales gas stream comprises the product gases;
collecting the hydrogen sulfide and the other gases in the acid gas stream;
introducing the acid gas stream to a sulfur recovery unit, where the acid gas stream comprises hydrogen sulfide;
introducing a sulfur recovery unit (SRU) air stream to the sulfur recovery unit, where the SRU air stream comprises oxygen;
introducing an SRU fuel stream to the sulfur recovery unit; and
reacting an amount of the hydrogen sulfide in the sulfur recovery unit with oxygen to produce an elemental sulfur stream and the tail gas stream.

19. The process of claim 1, further comprising the steps of:
introducing a sour gas feed to a gas sweetening unit, where the sour gas feed comprises hydrogen sulfide, product gases, and combinations of the same;
separating the hydrocarbons in the gas sweetening unit to produce a sales gas stream, where the sales gas stream comprises the product gases;
collecting the hydrogen sulfide and the other gases in the acid gas stream;
introducing the acid gas stream to a membrane unit, where the membrane unit comprises a hydrogen sulfide selective membrane;
separating the hydrogen sulfide from the acid gas stream in the membrane unit to produce a hydrogen sulfide rich acid gas and a hydrogen sulfide lean acid gas, where the hydrogen sulfide rich acid gas comprises hydrogen sulfide;
introducing the hydrogen sulfide rich acid gas to a sulfur recovery unit;
introducing a sulfur recovery unit (SRU) air stream to the sulfur recovery unit, where the SRU air stream comprises oxygen;
introducing an SRU fuel stream to the sulfur recovery unit;
reacting an amount of the hydrogen sulfide in the sulfur recovery unit with oxygen to produce an elemental sulfur stream and a tail gas stream;
mixing the tail gas stream and the hydrogen sulfide lean acid gas to produce a mixed gas stream; and
introducing the mixed gas stream to the CLC unit.

20. A system for recovering sulfur from a tail gas stream, the system comprising:
an air reactor, where the air reactor operates at an air reaction temperature and an air reaction pressure, where the air reactor comprises a fluidized bed reactor, where the fluidized bed comprises calcium carbonate;
an air reactor separator fluidly connected to the air reactor and a fuel reactor, where the air reactor separator comprises a solid-gas separation unit;
the fuel reactor fluidly connected to the air reactor separator, where the fuel reactor operates at a fuel reaction temperature and fuel reaction pressure, where the fuel reactor comprises a fluidized bed reactor, where the fluidized bed comprises calcium carbonate; and
a fuel reactor separator fluidly connected to the fuel reactor and the air reactor, where the fuel reactor separator comprises a solid-gas separation unit.

* * * * *